(12) United States Patent
Varghese et al.

(10) Patent No.: US 9,295,520 B2
(45) Date of Patent: Mar. 29, 2016

(54) HAIR DETECTOR WITH MULTIPLE FOCAL POINTS

(71) Applicant: KONINKLIJKE PHILIPS N.V., Eindhoven (NL)

(72) Inventors: Babu Varghese, Eindhoven (NL); Rieko Verhagen, Vught (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 14/357,077

(22) PCT Filed: Nov. 7, 2012

(86) PCT No.: PCT/IB2012/056213
§ 371 (c)(1),
(2) Date: May 8, 2014

(87) PCT Pub. No.: WO2013/068932
PCT Pub. Date: May 16, 2013

(65) Prior Publication Data
US 2014/0296837 A1 Oct. 2, 2014

Related U.S. Application Data

(60) Provisional application No. 61/558,005, filed on Nov. 10, 2011.

(51) Int. Cl.
*A61B 18/20* (2006.01)
*G01N 21/21* (2006.01)
(Continued)

(52) U.S. Cl.
CPC ............ *A61B 18/203* (2013.01); *A61B 5/0059* (2013.01); *A61B 5/448* (2013.01);
(Continued)

(58) Field of Classification Search
CPC .............. A61B 18/18; A61B 18/203; A61B 2018/00029; A61B 2018/0047; A61B 2018/202; A61B 2018/209; A61B 2018/216; A61B 2018/00476; A61B 2018/00601; A61B 2018/00642; A61B 2018/00785; A61B 2018/00904; A61B 2018/2025; A61B 5/0059; A61B 5/448; A61B 2017/00057; G01N 21/21; A61N 1/00; A61N 5/06
USPC .......... 606/9–13, 17, 18; 607/88–91; 128/898
See application file for complete search history.

(56) References Cited

U.S. PATENT DOCUMENTS

2010/0063491 A1* 3/2010 Verhagen ............. A61B 5/0066
606/9
2010/0188742 A1 7/2010 Chen et al.

FOREIGN PATENT DOCUMENTS

CN 10182064 A 10/2010
WO 2007039854 A1 4/2007
(Continued)

OTHER PUBLICATIONS

Varghese et al., "Contrast improvement in scattered light confocal imaging of skin birefringent structures by depolarization detection" J. Biophotonics 4, No. 11-12, 850-858 (Oct. 21, 2011).*

*Primary Examiner* — Gary Jackson
*Assistant Examiner* — Boniface N Nganga

(57) ABSTRACT

A hair treatment (40) device is provided comprising a light-based detector (10) for detecting a hair (22) near a skin surface (21) the detector (10) comprising a light source (11), optical elements (14, 16, 17, 18) and a polarization-sensitive light sensor (12, 13). The light source (11) is provided for generating a light beam (31) with an incident polarization. The optical elements (14, 16, 17, 18) are provided for focusing the light beam (31) at the hair (22) near the skin surface (21). The polarization-sensitive light sensor (12, 13) is provided for detecting light interacted with the hair (22) or the skin surface (21) and having a predefined linear polarization. The light source (11) and/or the optical elements (14, 16, 17, 18) are arranged to cause the light beam (31) to simultaneously have multiple spatially separated foci (51, 52, 53) at or near the hair (22) or the skin surface (21).

20 Claims, 3 Drawing Sheets

(51) Int. Cl.
  *A61B 5/00* (2006.01)
  *A61B 17/00* (2006.01)
  *A61B 18/00* (2006.01)
(52) U.S. Cl.
  CPC ...... *G01N 21/21* (2013.01); *A61B 2017/00057* (2013.01); *A61B 2018/00029* (2013.01); *A61B 2018/0047* (2013.01); *A61B 2018/00476* (2013.01); *A61B 2018/00601* (2013.01); *A61B 2018/00642* (2013.01); *A61B 2018/00785* (2013.01); *A61B 2018/00904* (2013.01); *A61B 2018/202* (2013.01); *A61B 2018/209* (2013.01); *A61B 2018/2025* (2013.01); *G01N 2021/216* (2013.01)

(56) References Cited

FOREIGN PATENT DOCUMENTS

| | | |
|---|---|---|
| WO | 2008120141 A2 | 10/2008 |
| WO | 2010106480 A1 | 9/2010 |
| WO | 2011121536 A1 | 10/2011 |

* cited by examiner

HAIR DETECTOR WITH MULTIPLE FOCAL POINTS

CROSS-REFERENCE TO PRIOR APPLICATIONS

This application is the U.S. National Phase application under 35 U.S.C. §371 of International Application No. PCT/IB2012/056213, filed on Nov. 7, 2012, which claims the benefit of U.S. Provisional Patent Application No. 61/558,005, filed on Nov. 10, 2011. These applications are hereby incorporated by reference herein.

FIELD OF THE INVENTION

This invention relates to a hair treatment device comprising a light-based detector for detecting a hair near a skin surface the detector comprising a light source, optical elements and a polarization-sensitive light sensor. The light source is provided for generating a light beam with an incident polarization. The optical elements are provided for focusing the light beam at the hair near the skin surface. The polarization-sensitive light sensor is provided for detecting light interacted with the hair or the skin surface and having a predefined linear polarization.

This invention further relates to a shaving device with a detector as described here before and to a method of detecting hairs near a skin surface.

BACKGROUND OF THE INVENTION

Such a hair treatment device is, e.g., known from the international patent application published as WO 2010/106480 A1. This patent application describes a device for imaging a hair near a skin surface of a body part. The device comprises a light source for generating a light beam with an incident polarization and a detector for detecting radiation returning from said hair. The detector has separate photodiodes for detecting light with the incident polarization and light with a polarization direction orthogonal to the incident polarization. The ratio of light intensities detected by the separate photodiodes is a probability measure for the presence of a hair at the tested skin location.

It has turned out that the sensitivity and specificity of this known detector is largely dependent on the angle between the polarization orientation of the incident light and the orientation of the hair to be detected and on the focusing depth inside the hair. Because the orientation of the hairs and the focusing depth inside the hair differs from hair to hair and over time, the hair-skin contrast obtained by the known detector is not entirely satisfactory.

Furthermore, the orientation of the hair in the plane perpendicular to the direction of light is a critical parameter that determines the sensitivity and specificity of hair detection. This in turn depends on the numerical aperture of the focusing element. With NA=0.9, the maximum detectable angle in the axial direction is limited to 30° whereas with NA=0.3, the maximum detectable is only 10°. In short, the hair is detected with optimal contrast when the illumination beam is focused at the desired depth inside the hair when it is brought within the detection cone.

OBJECT OF THE INVENTION

It is an object of the invention to provide a hair treatment device with an improved hair-skin contrast which is less dependent on the orientation and exact position of the hair to detect.

SUMMARY OF THE INVENTION

According to a first aspect of the invention, this object is achieved by providing a hair treatment device according to the opening paragraph, wherein the light source and/or the optical elements are arranged to cause the light beam to simultaneously have multiple spatially separated foci at or near the hair or the skin surface.

The multiple foci may be spatially separated in a direction lateral and/or axial with respect to the light beam. Different foci in the lateral direction hit the hair at different relative angles, causing the angle between the hair and the orientation of the incident polarization of the light beam to be different for the different foci. As a result, at any moment, the chance of at least one focus coming from a suitable relative angle for accurate hair detection is increased. For example, a transmission grating may be used for generating the multiple foci in the lateral direction. Alternatively, a plurality of light sources may be used for that purpose.

Different foci in the axial direction may coincide with the hair at different depths. Hair-skin contrast is optimal when the incident beam is focused at a depth of about 20-40 μm (micrometer). With multiple foci in the axial direction, the chance of at least one of them being at a suitable depth is increased. Different foci in the axial direction may, for example, be generated using multiple light beams with light of different wavelengths and/or divergence or by using a circular grating.

When the hair treatment device is moved over the skin surface in the axial direction, different focal points coincide with the same hair at different moments in time. The use of multiple measurements for detecting hairs does already provide an improved accuracy. In addition, the movement of the hair treatment device over the skin surface may change the relative angle between the hair and the skin surface and, therewith, the relative angle between the hair and the orientation of the incident polarization of the light beam. This effect does also contribute to the accuracy of the hair detection.

Additionally, the light source and/or the optical elements may be arranged to cause the light beam to have different orientations of incident polarization at the multiple foci. For example, a rotating laser source or a phase shifting element like a wave plate may cause the different incident polarizations. Such measures will further increase the chance of at least one focus coming from a suitable relative angle for accurate hair detection. The use of multiple spatially separated foci at the same moment in time is not only possible with linearly polarized light, but also with circularly or radially polarized light. In special embodiments, different foci may even have light with different types of polarization.

According to another aspect of the invention, a method for detecting a hair near a skin surface, the method comprising generating a light beam, focusing the light beam at a hair near the skin surface, and detecting light interacted with the hair or the skin surface and having a predefined linear polarization, wherein the generating and/or the focusing cause the light beam to have multiple foci at or near the hair or the skin surface.

These and other aspects of the invention are apparent from and will be elucidated with reference to the embodiments described hereinafter.

DETAILED DESCRIPTION OF THE INVENTION

Figure 1:
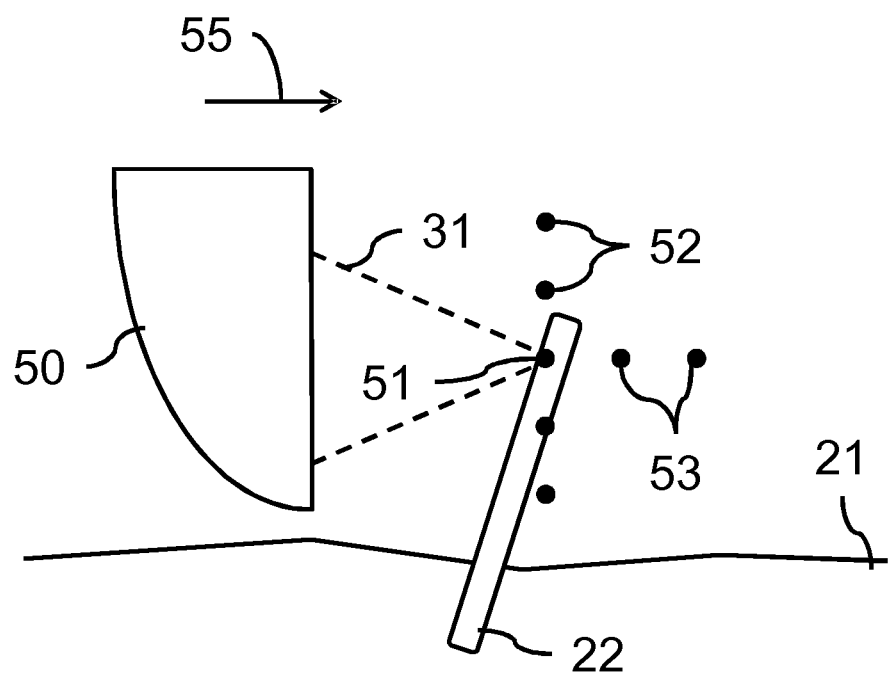
FIG. 1 shows an optical blade of a hair treatment device according to the invention, moving over a skin surface.

FIG. 1 shows an optical blade 50 of a hair treatment device according to the invention. In this figure, the optical blade 50 is moved over a skin surface 21 with a hair 22. In this example, the optical blade 50 is moved over the surface 21 in the direction of the arrow 55. The hair treatment device generates a light beam 31 for detecting hairs 22. The optical blade 50 directs the light beam 31 in a direction substantially parallel to skin surface 21 and focuses the light beam 31 in a first focal point 51. Instead of the optical blade 50 shown in this figure, other types of focusing elements, like microscope objectives and/or lenses may be used for directing and focusing the light beam 31. When the light of the light beam 31 interacts with, e.g., the hair 22 or skin surface 21, optical detection elements in the hair treatment device analyze the returning light and it is determined whether the focal point 51 did or did not coincide with a hair 22.

Experiments of the inventors have shown that an optimum contrast between hair 22 and skin 21 is realized when the focal point 51 lies about 20-40 μm inside the hair surface. When the optical blade 50 is moved along the skin surface 21, the focal point 51 may eventually reach this optimal position for detecting the hair 22. However, if the hair treatment device tests for the presence of hairs 22 periodically, the hair 22 may be missed. According to the invention, the hair treatment device may simultaneously provide additional focal points 53 in the axial direction, i.e. the direction of the incident light beam 31. The additional focal points 53 in the axial direction bring at least two important advantages. First, the additional focal points 53 increase the chance that at any moment in time one of the focal points 53 is focused at the optimum depth for detecting the hair 22. This increases the probability of detecting the hair 22. Additionally, different focal points 53 may hit the hair 22 at different moments in time, possibly under different relative angles. This increases the accuracy of the hair detection.

Also the relative angle between the hair 22 and the polarization orientation of the incident light beam 31 is important for obtaining a high hair-skin contrast. The polarization orientation of the incident beam 31 can be controlled by configuring the light source and the optical elements inside the hair treatment device. The orientation of the hairs 22 varies from hair to hair and over time. Also the orientation of the optical blade 50 relative to the skin surface 21 may vary over time. According to the invention, different angles of incidence may be used to simultaneously create multiple focal points 52 in the lateral direction, i.e. in the plane perpendicular to the light beam 31. When the different foci 52 make different relative angles with respect to the hair 22, the chance of at least one of the foci 52 providing a suitable angle for accurate hair detection is increased. Additionally, the laser source and optical elements of the hair treatment device may provide different orientations of incident polarization for the different lateral and/or axial foci 52, 53. This may, e.g., be realized by rotating the laser source or using phase shifting elements, such as wave plates. The use of multiple spatially separated foci 51, 52, 53 at the same moment in time is not only possible with linearly polarized light, but also with circularly or radially polarized light. In special embodiments, different foci 51, 52, 53 may even have light with different types of polarization.

Figure 2:
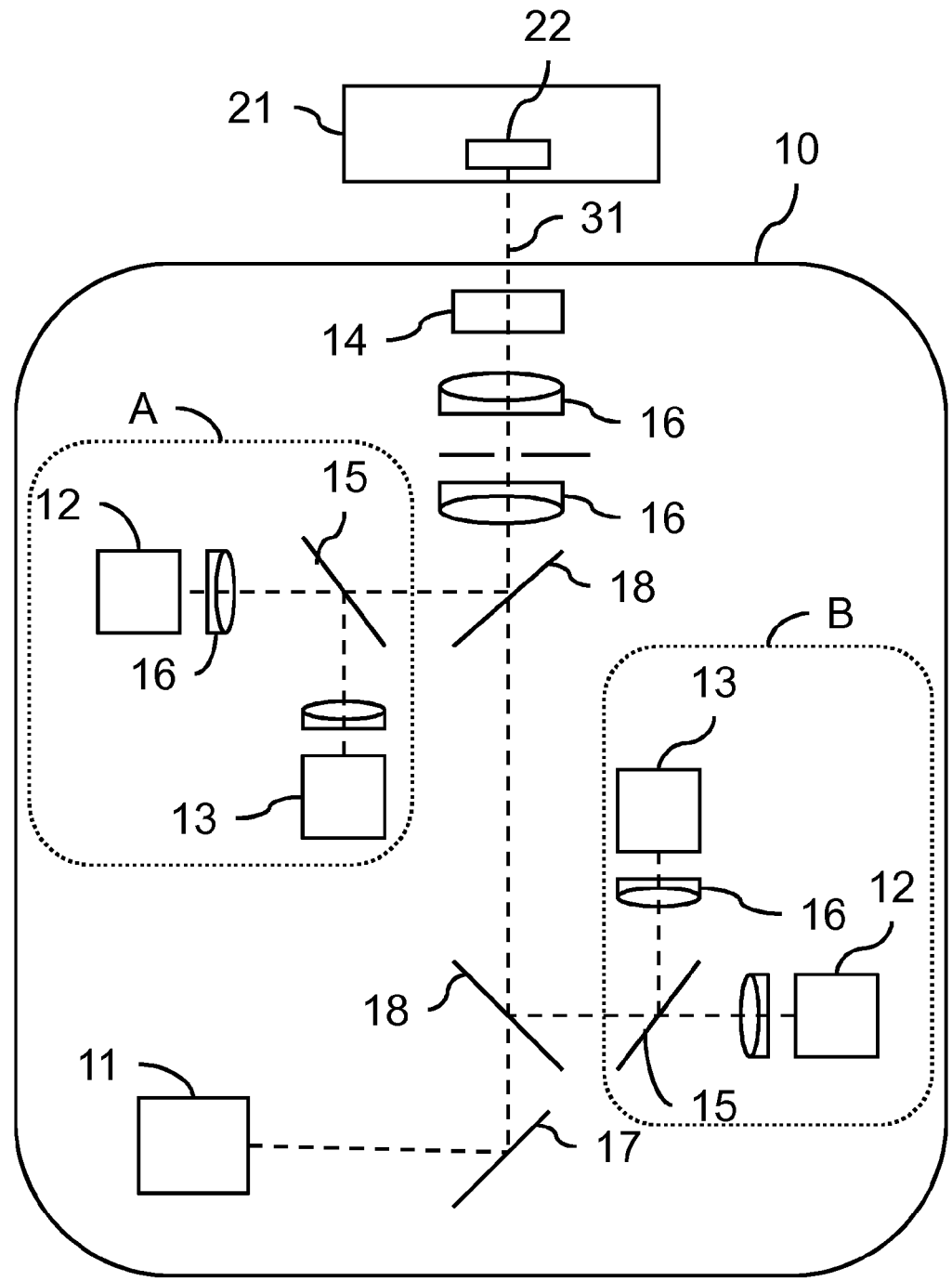
FIG. 2 shows a block diagram of a light-based detector according to the invention, and FIG. 3 schematically shows a shaving device according to the invention.

FIG. 2 shows a block diagram of a light-based detector 10 according to the invention. For example, the detector 10 according to the invention may be adapted to detect hairs 22 on human or animal skin 21. Hair detection may be useful in, IPL (Intense Pulsed Light) based or laser based shaving apparatuses. Alternatively, the detector 10 may be adapted to detect collagen in human or animal skin 21 for determining skin elasticity. The light-based detector 10 of FIG. 2 comprises a laser source 11 for emitting a laser beam, preferably in the near-infrared or infrared part of the spectrum. For example, light with a wavelength of 785 or 850 nm may be used. Optical elements, like lenses 16 and/or mirrors 17 focus the light beam 31 on the skin 21. A control unit (not shown) coupled to the laser source 11 and/or (part of) the optical elements 16, 17 controls the exact optical path of the laser beam in order to control the exact area of skin 21 that is tested for the presence of a hair 22 and to enable scanning lines or 2D areas of skin 21.

The additional foci 52, 53 may, e.g., be generated by using a diffraction grating 14. Additional lateral focal points 52 may be generated by a transmission grating and additional axial focal points 53 may be generated by a circular grating. Alternatively or additionally, multiple wavelengths or multiple beams with different divergence or sent out in slightly different directions may be used for generating the additional foci 52, 53. Additional foci 52, 53 may also be provided by, e.g., holographic lenses.

When the light beam 31 interacts with the skin surface 21 or the hair 22, the returning beam re-enters the detector 10. The optical elements 16, 17, 18 lead the returning beam to light sensors or photo diodes 12, 13. For example semitransparent mirrors and/or polarizing beam splitters may be used for providing different light paths for the outgoing and the returning light beams. In a typical embodiment, separate detection blocks A, B are used for detecting different polarization components in the returning light beam. The ratio between the signals for the incident polarization and for the orthogonal polarization may be used for determine when a hair 22 is detected.

Beam splitters 15 split the returning beams and lead the split beams to different photo diodes 12, 13 for separately collecting information from the different foci 52, 53. If light of different wavelengths is used for generating the additional focal points, the beam splitter 15 may, e.g., be a dichroic beam splitter or a standard beam splitter with filters with a specific transmission band width for the illumination wavelength.

Figure 3:
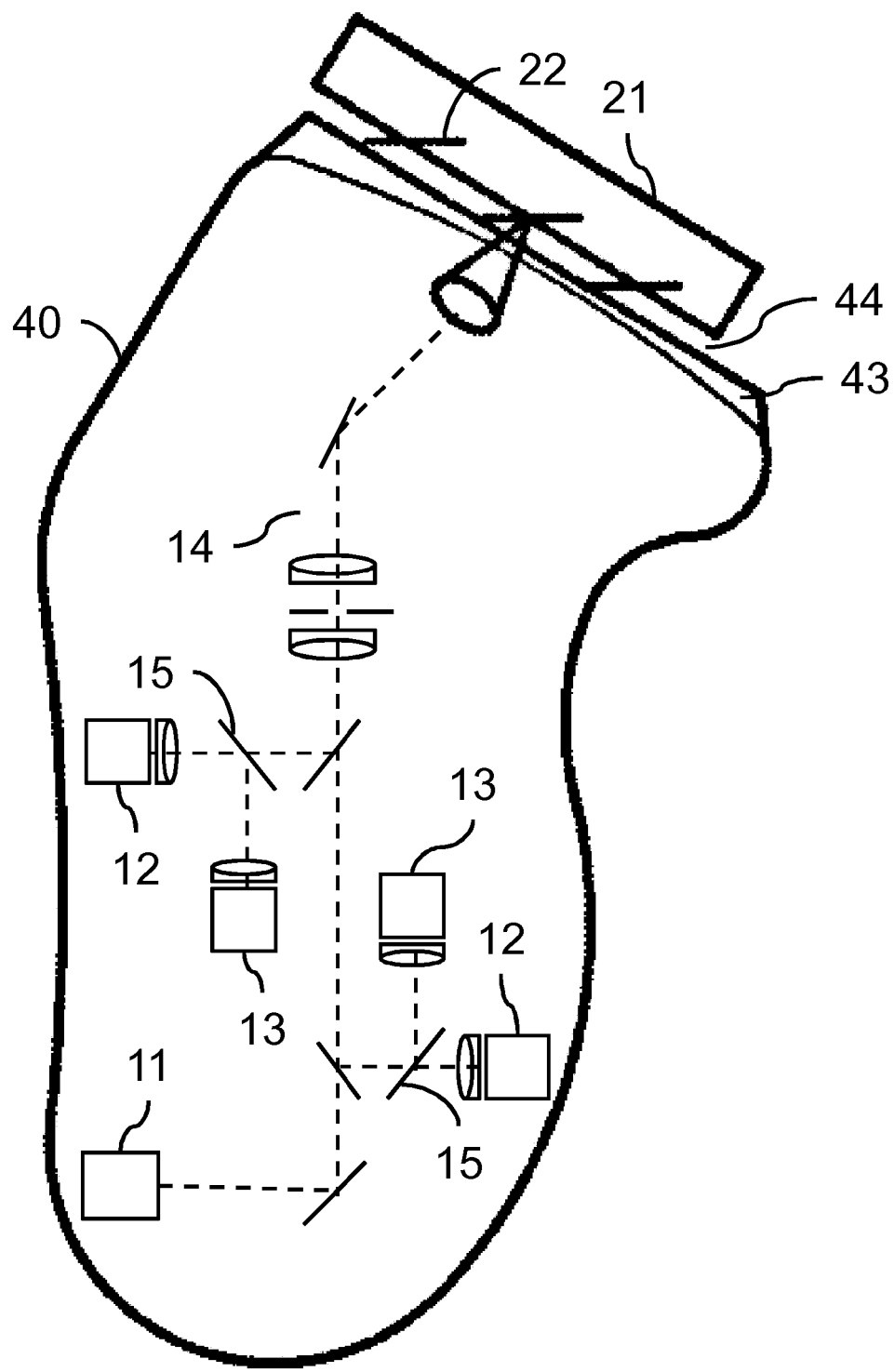

FIG. 3 schematically shows a shaving device 40 according to the invention. The shaving device 40 comprises a hair detector similar to the one described above with reference to FIG. 2. Equal reference numbers correspond to similar features. In addition to features already discussed above, the shaving device 40 may also comprise an optical or contact window 43 and an immersion fluid 44 for improving the penetration properties of the radiation into the skin 21. For example, the fluid 84 may be an index matching fluid, having an index of refraction which is halfway between that of the optical window and that of the skin 21. Preferably, all refractive indices are substantially equal. This also lowers the reflection from the skin 21. The fluid 44 may also be selected for the purpose of cooling the skin 21, or treating it otherwise. Furthermore, although the contact window 43 is optional, it helps in serving as a reference for determining positions of skin objects, such as the hairs 22.

The shaving device 40 may not only use the laser source 11 for detecting the hair 22, but also for cutting it. When the laser source 11 is used for cutting, it may operate at a different power level than when detecting hairs 22. Alternatively, a separate laser source (not shown) is used for the cutting of the hairs 22. The control over the cutting process may be performed by the control unit or by an additional cutting processor (not shown). The cutting processor is coupled to the light based detector 10 to activate the hair-cutting laser source in a focal position of the hair-cutting laser beam near the skin surface 21 in which the light-based detector has detected the presence of a hair 22.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A hair treatment device comprising a light-based detector for detecting a hair near a skin surface, the detector comprising:
   a light source for generating a light beam with an incident polarization,
   optical elements for focusing the light beam at the hair near the skin surface, and
   a polarization-sensitive light sensor for detecting light interacted with the hair or the skin surface and having a predefined linear polarization,
   wherein the light source and the optical elements are arranged to cause the light beam to simultaneously have multiple spatially separated foci in a lateral direction and in an axial direction at or near the hair or the skin surface and
   wherein the light source and the optical elements are arranged to cause the light beam to have different orientations of incident polarization at the multiple foci.

2. A hair treatment device as claimed in claim 1, wherein the optical elements are arranged to cause the light beam to have the multiple foci spatially separated in a lateral direction with respect to the light beam.

3. A hair treatment device as claimed in claim 2, wherein the optical elements comprise a transmission grating.

4. A hair treatment device as claimed in claim 1, wherein the light source is arranged to cause the light beam to have the multiple foci spatially separated in an axial direction with respect to the light beam.

5. A hair treatment device as claimed in claim 1, wherein the light source is operative to generate multiple light beams with light of different wavelengths.

6. A hair treatment device as claimed in claim 1, wherein the light source is operative to generate multiple light beams with different divergence.

7. A hair treatment device as claimed in claim 1, wherein the optical elements comprise a circular grating.

8. A hair treatment device as claimed in claim 1, wherein the light source and/or the optical elements are arranged to cause the light beam to have different types of incident polarization at the multiple foci.

9. A hair treatment device as claimed in claim 1, wherein the polarization-sensitive light sensor comprises separate photodiodes for collecting information from light from respective foci.

10. A hair treatment device according to claim 1, the device further comprising a hair-cutting laser source for generating a hair-cutting laser beam and a processor which is coupled to the light-based detector, wherein the processor is arranged to activate the hair-cutting laser source in a focal position of the hair-cutting laser beam near the skin surface in which the light-based detector has detected the presence of the hair.

11. A method for detecting a hair near a skin surface, the method comprising:
   generating a light beam, via a light source, with an incident polarization,
   focusing the light beam, via optical elements, at a hair near the skin surface, and
   detecting light interacted with the hair or the skin surface, via a polarization-sensitive light sensor, and having a predefined linear polarization,
wherein the generating, via the light source, and the focusing, via the optical elements, causes the light beam to simultaneously have multiple spatially separated foci in a lateral direction and in an axial direction at or near the hair or the skin surface and to have different orientations of incident polarization at the multiple foci, wherein different foci are arranged to coincide with the same hair.

12. The method as claimed in claim 11, wherein the optical elements are arranged to cause the light beam to have the multiple foci spatially separated in a lateral direction with respect to the light beam.

13. The method as claimed in claim 12, wherein the optical elements comprise a transmission grating.

14. The method as claimed in claim 11, wherein the light source is arranged to cause the light beam to have the multiple foci spatially separated in an axial direction with respect to the light beam.

15. The method as claimed in claim 11, wherein the light source is operative to generate multiple light beams with light of different wavelengths.

16. The method as claimed in claim 11, wherein the light source is operative to generate multiple light beams with different divergence.

17. The method as claimed in claim 11, wherein the optical elements comprise a circular grating.

18. The method as claimed in claim 11, wherein the light source and/or the optical elements are arranged to cause the light beam to have different orientations of incident polarization at the multiple foci.

19. The method as claimed in claim 11, wherein the polarization-sensitive light sensor comprises separate photodiodes for collecting information from light from respective foci.

20. The method as claimed in claim 11, further comprising:
   generating a hair-cutting laser beam, via a hair-cutting laser source, and
   activating the hair-cutting laser source in a focal position of the hair-cutting laser beam near the skin surface in which the light-based detector has detected the presence of the hair, via a processor which is coupled to the light-based detector.

* * * * *